United States Patent
Jost

(10) Patent No.: US 9,433,937 B2
(45) Date of Patent: Sep. 6, 2016

(54) WATER-INSOLUBLE RUTHENIUM CATALYST COMPOSITION FOR USE IN AQUEOUS HYDROGENATION REACTIONS

(71) Applicant: Dexlechem GMBH, Berlin (DE)

(72) Inventor: Sonja Jost, Berlin (DE)

(73) Assignee: DEXLECHEM GMBH, Berlin (DE)

( * ) Notice: Subject to any disclaimer, the term of this patent is extended or adjusted under 35 U.S.C. 154(b) by 0 days.

(21) Appl. No.: 14/772,393

(22) PCT Filed: Mar. 5, 2014

(86) PCT No.: PCT/EP2014/054291
§ 371 (c)(1),
(2) Date: Sep. 3, 2015

(87) PCT Pub. No.: WO2014/135605
PCT Pub. Date: Sep. 12, 2014

(65) Prior Publication Data
US 2016/0008803 A1 Jan. 14, 2016

(30) Foreign Application Priority Data
Mar. 6, 2013 (EP) ..................................... 13157998

(51) Int. Cl.
*C07C 29/145* (2006.01)
*B01J 31/24* (2006.01)
*C07C 67/31* (2006.01)
*C07F 15/00* (2006.01)

(52) U.S. Cl.
CPC ......... *B01J 31/2457* (2013.01); *B01J 31/2409* (2013.01); *C07C 29/145* (2013.01); *C07C 67/31* (2013.01); *C07F 15/0046* (2013.01); *B01J 2231/643* (2013.01); *B01J 2531/0266* (2013.01); *B01J 2531/821* (2013.01); *B01J 2531/90* (2013.01); *B01J 2531/96* (2013.01); *C07B 2200/07* (2013.01)

(58) Field of Classification Search
CPC .......................... B01J 31/2457; C07C 29/145
See application file for complete search history.

(56) References Cited

U.S. PATENT DOCUMENTS 6,184,413 B1 2/2001 Davis et al.
2007/0149831 A1 6/2007 Amano et al.

OTHER PUBLICATIONS

Wolfson, A. et al.: "The role of the solvent in the asymmetric hydrogenation of beta-keto esters with Ru-BINAP", Journal of Molecular Catalysis A: Chemical, vol. 198, 2003, pp. 39-45.
Duprat De Paijle S et al: "SYNPIIOS(R), a new chiral diphosphine ligand: synthesis, molecular modeling and application in asymmetric hydrogenation",Tetrahedron Letters,Elsevier,Amsterdam, NL, vol. 44, No. 4, Jan. 20, 2003, pp. 823-826.
Touati R et al: "Synthesis of enantiopure (R)-(-) massoialactone through ruthenium-SYNPHOS<(>R) asymmetric hydrogenation", Tetrahedron Asymmetry,Pergamon Press Ltd, Oxford, GB, vol. 17, No. 24, Dec. 27, 2006, pp. 3400-3405.

*Primary Examiner* — Golam M M Shameem
(74) *Attorney, Agent, or Firm* — JMB Davis Ben-David

(57) ABSTRACT

The invention relates to a method for converting a precatalyst complex to an active catalyst complex, wherein the precatalyst complex and the active catalyst complex comprise a ruthenium atom and an optically active ligand that is insoluble in water, and the active catalyst complex furthermore comprises a monohydride and a water molecule. The method comprises the steps of providing water as an activation solvent system with a pH value equal or below 2, and solving said precatalyst complex, an acid, and hydrogen therein. The invention further relates to a method for manufacturing a catalyst composition, a method for hydrogenating a substrate molecule and a reaction mixture.

4 Claims, No Drawings

WATER-INSOLUBLE RUTHENIUM CATALYST COMPOSITION FOR USE IN AQUEOUS HYDROGENATION REACTIONS

CROSS-REFERENCE TO RELATED APPLICATIONS

This is the U.S. National Stage of International Application No. PCT/EP2014/054291, filed Mar. 5, 2014, which was published in English under PCT Article 21(2), which in turn claims the benefit of EP Patent Application No. 13157998.9, filed Mar. 6, 2013.

The present invention relates to a method for converting an inactive ruthenium precatalyst into an active catalyst in aqueous solutions. The present invention further relates to a method for manufacturing a water-insoluble chiral catalyst, and to its use.

Pure enantiomers are used in the synthesis of, inter alia, pharmaceuticals, agrochemicals, flavours and fragrances. Asymmetric chemocatalysis is an efficient production method for chiral molecules. Current large-scale protocols, however, rely on the use of organic solvents, making these methods expensive and problematic from a safety and environmental impact point of view.

Chiral noble-metal complexes in aqueous solutions are known in the art. Kan-To Wan et al. (Tetrahedron Asymmetry, Pergamon Press Ltd, Oxford, GB, pages 2461-2467, 1 Jan. 1993) shows a sulfonated ruthenium BINAP (Binaphtalendiyl-bis[diphenylphosphine) complex. WO2007104690 shows a ruthenium phosphine complex. U.S. Pat. No. 5,827,794 shows a sulfonated ruthenium BINAP complex.

Asymmetric synthesis employing metal catalysts with chiral ligands are described in U.S. Pat. No. 5,324,870, which shows the use of a chiral ruthenium phosphine complex in hydrogenation reactions, in Touati et al. (Tetrahedron Asymmetry, Pergamon Press Ltd, Oxford, GB, pages 3400-3405, 27 Dec. 2006), which shows asymmetric hydrogenation reactions catalysed by a ruthenium SYNPHOS complex, in Duprat et al. (Tetrahedron Letters, 44(4), pages 823-826, 2003), which shows a ruthenium SYNPHOS complex, and in WO9215400 which shows a ruthenium BINAP complex.

In summary, known methods for asymmetric catalysis use organic solvents. Water is a desirable solvent for conducting asymmetric syntheses with ruthenium catalysts, particularly in view of technical-scale applications.

Rhodium-catalyzed asymmetric hydrogenations of different substrates in aqueous/surfactant media and/or biphasic systems have been explored by Grassert et al. (J. Organomet. Chem., 621, pages 158-165, 2001) they show a 1,5-cyclooctadiene)bismethylallylrhodium phosphine complex.

The ligands used in aqueous solutions differ from conventional chiral ligands—which are insoluble in water—by the addition of chemical groups to render them water soluble. This modification is expensive.

The ability to use water-insoluble chiral ligands in aqueous phase catalysis would be of advantage. To the knowledge of the present inventors, however, chiral synthesis employing chiral water-insoluble ruthenium containing catalysts in aqueous media has not been accomplished so far.

Based on this background, it is the objective of the present invention to provide means and methods for chiral hydrogenation reactions in aqueous media.

Surprisingly it was found that under conditions of low pH, water-insoluble catalysts can be made and used in aqueous media, particularly in the absence of any organic solvent. It was further found that such catalyst can be activated in aqueous media.

The present invention provides a method for converting a precatalyst complex to an active catalyst complex, wherein the precatalyst complex comprises a ruthenium atom and an optically active ligand, and wherein the active catalyst complex comprises the ruthenium atom, the optically active ligand, a monohydride and at least one water molecule, and wherein the monohydride and the water molecule are bound to said ruthenium atom, and wherein the optically active ligand is insoluble in water. The nature of the bond between the ruthenium atom and the water molecule or the monohydride is covalent or coordinative in nature. The method of the invention comprises the steps of providing water as an activation solvent system, and solving the precatalyst complex an acid, and hydrogen in the activation solvent system at a pH value of the activation solvent system equal or below 2.

According to a first aspect of the invention, a method for converting a precatalyst complex to an active catalyst complex is provided,
  wherein the precatalyst complex and the active catalyst complex comprise a ruthenium atom and an optically active ligand that is insoluble in water, and
  wherein the active catalyst complex furthermore comprises a monohydride and a water molecule,
  the method comprising the steps of:
  a) providing water as an activation solvent system,
  b) adding to, particularly solving in, said activation solvent system:
    the precatalyst complex,
    a solubilizer,
    an acid, and
    hydrogen,
  characterized in that the final pH value of the activation solvent system is equal or below 2 after addition of the acid.

The monohydride and the water molecule are bound to the ruthenium atom.

A precatalyst complex in the context of the present specification refers particularly to a complex comprising an optically active ligand that (the ligand) is insoluble in water, a ruthenium atom, and optionally a solvent molecule selected from an organic polar solvent and water, whereby the solvent molecule is bound to the ruthenium atom. Such precatalyst complex is not able to hydrogenate a double bond selected from $C=O$ and $C=N$ in a substrate molecule; particularly the double bond cannot be hydrogenated in absence of a monohydride bound to the ruthenium atom; likewise, in a precatalyst, the solvent molecule bound to the ruthenium atom is not substitutable against a substrate molecule in an aqueous solvent system.

An active catalyst complex in the context of the present specification refers particularly to a compound comprising an optically active ligand that (again, the ligand) is insoluble in water, a ruthenium atom, at least one water molecule and a monohydride being bound to the ruthenium atom. Such active catalyst complex is configured to reduce a double bond selected from $C=O$ and $C=N$ in a substrate molecule, the monohydride serving as the reducing agent. Without wishing to be bound by theory, it appears that the solvent molecule can be substituted by the substrate molecule mentioned above in an aqueous solvent system, and one half of the substrate molecule's double bond is hydrogenated by the monohydride, while the other half of the double bond may be hydrogenated by elementary hydrogen solved in the solvent system, wherein the hydrogenation is performed. The inventors hypothesize, again without wishing to be bound by theory, that the underlying mechanism involves blocking of the catalytic complex by water molecules at neutral pH.

An optically active ligand in the context of the present specification refers to a compound that is capable of binding to the ruthenium atom described above and is characterized by an optical activity, wherein optical activity or optical rotation is the turning of the plane of linearly polarized light as the light travels through the ligand. Accordingly, there are at least two enantiomeric forms of the optically active ligand, wherein each form rotates the plane of light in an opposite direction.

The term "insoluble in water" in the context of the present specification particularly refers to a solubility of an entity of below 0.02 mol/l, 0.01 mol/l, 0.005 mol/l or 0.001 mol/l at 25° C.

A monohydride in the context of the present specification refers to a hydrogen atom with one electron, whereby this electron participates in the bonding between the hydrogen atom and the ruthenium atom, while the other electron of the bond is provided by the ruthenium atom.

A solubilizer in the context of the present specification refers to a compound or composition, the presence of which increases the solubility in water of poorly soluble or non-soluble compounds or compositions. In some embodiments, the solubilizer is a non-ionic surfactant or an organic solvent that is miscible with water.

In some embodiments, the activation solvent system comprises at least (≥)25% (v/v), ≥50% (v/v), ≥75% (v/v), ≥80% (v/v), ≥90% (v/v), ≥99% (v/v) or 100% (v/v) water.

In some embodiments, the precatalyst complex comprises a monohydride bound to the ruthenium complex. Such precatalyst complex with bound monohydride can be converted to an active catalyst complex by the method for converting a precatalyst complex to an active catalyst complex according to the invention, with the exception that the method may be performed without solving hydrogen in the activation solvent system.

In some embodiments, the acid is characterized by a pKa value of <0.

In some embodiments, the acid is a hydrogen acid. In some embodiments, the acid is characterized by formula HX, wherein X is the corresponding anionic base.

In some embodiments, the acid deprotonates after solving in the activation solvent system, whereby the resulting corresponding anionic base of the acid binds to the ruthenium atom. The nature of the bond between the ruthenium atom and the corresponding anionic base is covalent or coordinative in nature.

In some embodiments, the acid is selected from the group comprised of sulphuric acid, nitric acid, sulfonic acid, perchloric acid, perbromic acid, fluorosulfuric acid, hydrobromic acid, hydrochloric acid, hydriodic acid and fluoroboric acid.

In some embodiments, an acid solution is solved in the activation solvent system, wherein the acid solution is characterized by an acid concentration of 0.05 N, 0.1 N, 0.2 N, 0.3 N, 0.4 N, 0.5 N, 0.6 N, 0.7 N, 0.8 N, 0.9 N, 1 N, 1.5 N, 2 N, 2.5 N or 3 N.

In some embodiments, the optically active ligand is a bidentate ligand or a monodentate ligand.

In some embodiments, one bidentate ligand is bound to the ruthenium atom. In some embodiments, two monodentate ligands are bound to the ruthenium atom. The nature of the bond between the ruthenium atom and the monodentate ligand or the bidentate ligand is covalent or coordinative in nature.

In some embodiments, the catalyst complex is characterized by two water molecules bound to the ruthenium atom.

In some embodiments, the precatalyst complex is characterized by formula I

wherein $L_1$ and $L_2$ are independently from another a monodentate optically active ligand, or $L_1$ and $L_2$ together form a bidentate optically active ligand, S is an organic solvent molecule comprising 1, 2, 3, 4, 5, 6, 7 or 8 carbon atoms and optionally at least one oxygen atom, or a water molecule, $R^1$ is F, Cl, Br, I, $BF_4$, $SO_3F$, $ClO_4$, $SO_4$, $NO_3$, actetate or cymene.

$R^2$ is a hydrogen (monohydride) or $R^1$.

In some embodiments, the organic solvent molecule is selected from methanol, trichloromethane, dichloromethane, ethanol, trifluoroethanol, n-propanol, 2-propanol, n-butanol, 2-butanol, n-pentanol, 2-pentanol, 3-pentanol, n-hexanol, 2-hexanol, 3-hexanol, hexane, heptane and octane.

In some embodiments, the active catalyst complex is characterized by formula II

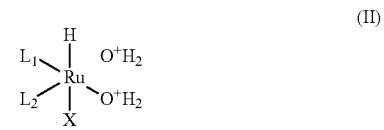

wherein $L_1$, $L_2$ have the same meaning as described above, and X is $R^1$ described above or the corresponding anionic base to the acid HX described above.

In some embodiments, the water molecule bound to the ruthenium leaves the catalyst as oxonium ($H_3O^+$), when being substituted against the substrate molecule.

Such active catalyst complex is suitable to perform a catalytic cycle, wherein at least one water molecule bound to the ruthenium atom are substituted by a substrate molecule comprising a double bond selected from C=O and C=N, one partner of the double bond is hydrogenated by the monohydride bound to the ruthenium atom, the other partner is hydrogenated by a monohydride from elementary hydrogen, the hydrogenated substrate molecule is cleaved off the ruthenium atom and a monohydride binds to the ruthenium atom thereby regenerating the active catalyst complex.

In some embodiments, the optically active ligand is selected from the group comprised of:

Synphos (5,5'-bis(diphenylphosphino)-4,4'-bi-1,3-benzo-dioxane)

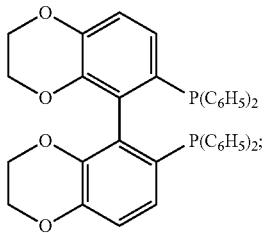

Segphos (5,5'-bis(diphenylphosphino)-4,4'-bi-1,3-benzo-dioxole):

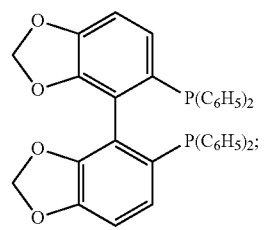

BINAP (2,2'-bis(diphenylphosphino)-1,1'-binaphthyl)

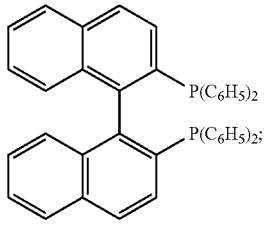

DIOP (O-isopropyliden-2,3-dihydroxy-1,4-bis(diphenyl-phosphino)butane):

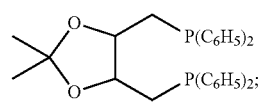

DIPAMP (ethane-1,2-diylbis[(2-methoxyphenyl)phenyl-phosphane]):

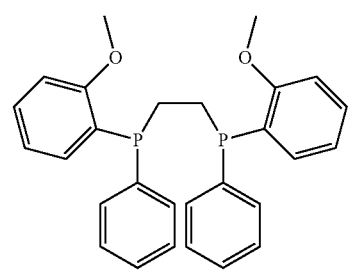

CHIRAPHOS (bis(diphenylphosphino)butane):

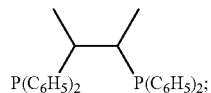

NORPHOS ((3-diphenylphosphanyl-2-bicyclo[2.2.1]hept-5-enyl)-diphenyl-phosphane):

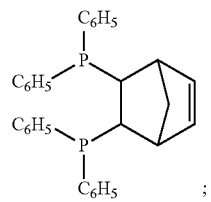

DEGUPHOS ((1-benzyl-4-diphenylphosphanyl-pyrroli-din-3-yl)-diphenyl-phosphane):

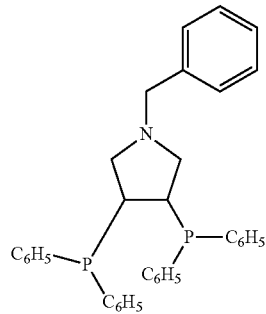

PROPHOS ((2-diphenylphosphanyl-1-methyl-ethyl)-di-phenyl-phosphane):

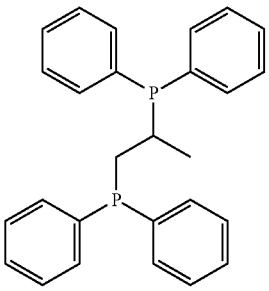

DIMPC ([2-(diphenylphosphanylmethyl)cyclohexyl]methyl-diphenyl-phosphane):

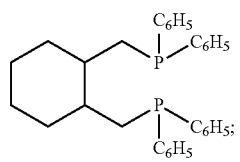

BPPM (tert-butyl 4-benzhydryl-2-(2,2-diphenylethyl)pyrrolidine-1-carboxylate):

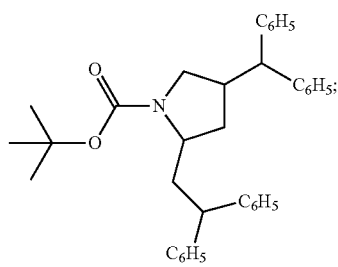

BNPE ([2-(1-naphthyl)phenyl]-[2-[2-(1-naphthyl)phenyl]phosphanylethyl]phosphane):

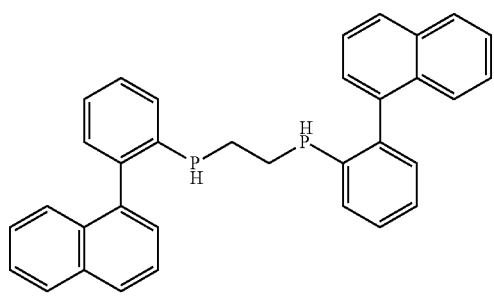

MeO-BIHEP ([2-(2-diphenylphosphanyl-6-methoxy-phenyl)-3-methoxy-phenyl]-diphenyl-phosphane):

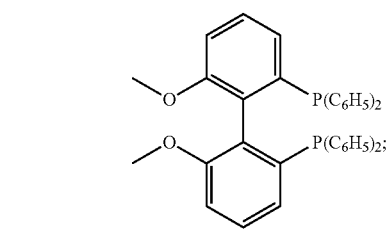

Cl-MeO BIHEP ([4-chloro-2-(3-chloro-6-diphenylphosphanyl-2-methoxy-phenyl)-3-methoxy-phenyl]-diphenyl-phosphane):

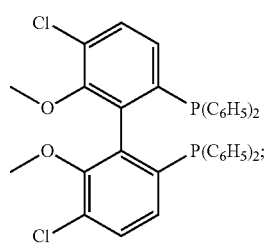

Cl-MeO-BIHEP ([5-chloro-2-(4-chloro-2-diphenylphosphanyl-6-methoxy-phenyl)-3-methoxy-phenyl]-diphenyl-phosphane):

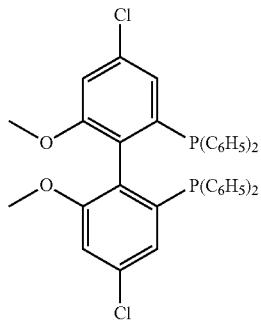

HEXAPHEMP ([2-(6-diphenylphosphanyl-2,3,4-trimethyl-phenyl)-3,4,5-trimethyl-phenyl]-diphenyl-phosphane:

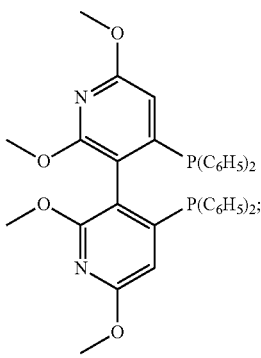

P-PHOS ([3-(4-diphenylphosphanyl-2,6-dimethoxy-3-pyridyl)-2,6-dimethoxy-4-pyridyl]-diphenyl-phosphane):

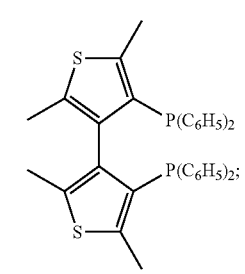

TMBTP ([4-(4-diphenylphosphanyl-2,5-dimethyl-3-thienyl)-2,5-dimethyl-3-thienyl]-diphenyl-phosphane):

SOLPHOS ([8-(7-diphenylphosphanyl-4-methyl-2,3-dihydro-1,4-benzoxazin-8-yl)-4-methyl-2,3-dihydro-1,4-benzoxazin-7-yl]-diphenyl-phosphane):

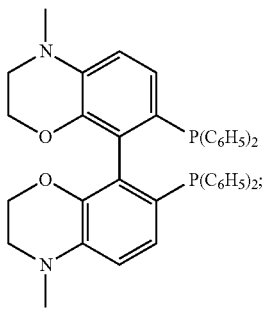

a compound characterized by formula Ill:

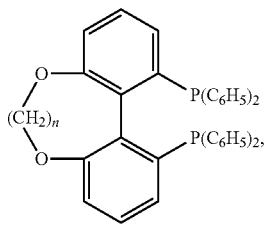

wherein n is 1, 2, 3, 4, 5 or 6.

In some embodiments, the solubilizer is a polar organic solvent or a surfactant that is capable of forming micelles in water and is resistant to hydrolysis at pH≤2.

In some embodiments, the solubilizer is a non-ionic surfactant, particularly an alkylglycoside, more particularly D-Glycopyranoside C9-C11 alkyl (CAS No. 132778-08-6, obtained from Cognis/BASF AG).

A surfactant in the context of the present specification refers to an amphiphilic compound that lowers the surface tension of a liquid, particularly of water.

A micelle in the context of the present specification refers to a supramolecular spherical aggregate of surfactant molecules dispersed in a liquid, particularly in water. Such aggregate exhibits a hydrophilic surface that is in contact to the liquid and formed by hydrophilic heads of the surfactant molecules and a lipophilic or hydrophobic core that is shielded from the liquid and formed by the lipophilic tail group of the surfactant molecules.

In some embodiments, the surfactant is a detergent or tenside comprising a hydrophilic head group and a lipophilic tail group.

In some embodiments, the hydrophilic head group is an anionic group, wherein the anionic group does not comprise a double bound.

In some embodiments the hydrophilic head is a non-ionic group selected from the group comprised of fatty alcohols, polyoxyethylene glycol alkyl ethers, polyoxypropylene glycol alkyl ethers and glucosides.

In some embodiments, the hydrophilic head is a cationic group select from tetraalkylammonium and quaternary ammonium cations.

In some embodiments, the lipophilic tails group consists of hydrocarbons.

In some embodiments, the lipophilic head is selected from a $C_3$-$C_{30}$-alkyl, -aryl, -heterocyclyl, -heteroaryl and -carbocyclyl.

The term alkyl or alkyl group in the context of the present specification signifies a saturated hydrocarbon moiety, which may be linear, branched, cyclic or cyclic with linear or branched side chains. The term alkyl includes partially unsaturated hydrocarbons such as propenyl. Examples are n- or isobutyl, n- or cyclohexyl, heptyl, octyl, dodecyl and octadecyl. The term alkyl may extend to alkyl groups linked or bridged by hetero atoms such as N, S or O.

The term aryl in the context of the present specification signifies a cyclic aromatic hydrocarbon. Heteroaryl in the context of the present invention are aryls that comprise nitrogen, oxygen or sulfur atoms. Examples of heteroarly are pyrrol, 1,2- or 1,3-diazole, thiadiazole (e.g. 1,2,5-, 1,2,3-), furane, thiophene, indole and its O- and S-homologues, indolizine or pyridine.

The term heterocyclyl in the context of the present specification signifies chains or rings, or combinations thereof, of carbon, oxygen, nitrogen and/or sulphur atoms that are connected by single or double bonds. Examples for heterocyclyl moieties are a morpholino moiety and a piperidinyl moiety.

The term carbocyclyl in the context of the present specification signifies rings of carbon or a combination of chains and rings of carbon that are connected by single bonds. Examples for carbocyclyls are cyclopropane, cyclobutane, cyclopentane, cyclohexane and cycloheptane.

In some embodiments, the surfactant has a decomposition rate constant at pH 2 of not higher than $10\ s^{-1}$, $1\ s^{-1}$, $0.1\ s^{-1}$, $0.01\ s^{-1}$ or $0.001\ s^{-1}$ at 25° C.

In some embodiments, the surfactant is non-ionic. A non-ionic surfactant in the context of the present specification refers particularly to a surfactant without dissociative groups, particularly without a carboxy group.

In some embodiments, the surfactant is an alkylglycoside. An alkylglycoside in the context of the present specification refers to a compound comprising a $C_1$-$C_{20}$ alkyl alcohol moiety as lipophilic tail group and a sugar moiety as hydrophilic head group, wherein the anomeric hydroxyl group of the sugar and the hydroxyl group of the alcohol form an actetal bond.

In some embodiments, the surfactant is the alkylglycoside D-Glycopyranoside C9-C11 alkyl (CAS No. 132778-08-6).

In some embodiments, the lipophilic tail group is a $C_8$-$C_{14}$ alkyl alcohol moiety.

In some embodiments, the sugar moiety comprises a monosaccharide or an oligosaccharide.

In some embodiments, the monosaccharide is selected from glucose, fructose, mannose, ribose, galactose and ribulose.

In some embodiments, the oligosaccharide is selected from sucrose, maltose, cellobiose or raffinose.

In some embodiments, the surfactant has a critical micellar concentration (CMC) value of ≤10 mM, more preferably ≤1 mM, most preferably ≤0.25 mM, wherein CMC specifies the lowest concentration of the surfactant in water at which spherical micelles are formed at 25° C. and 1 bar.

In some embodiments, the surfactant is provided in the activation solvent system in a concentration equal or above the surfactant's critical micelle concentration.

According to a second aspect of the invention, a method for obtaining a catalyst composition is provided, comprising the steps of:
a) providing water as a preparation solvent system, and
b) adding to, particularly solving in, the preparation solvent system:
a first catalyst composition comprising an optically inactive ligand and a ruthenium atom, an optically active ligand, wherein the optically active ligand is insoluble in water,
a solubilizer, and
an acid,
there by the optically inactive ligand in the first catalyst composition is substituted by the optically active ligand yielding a second catalyst composition comprising the ruthenium atom and the optically active ligand, characterized in that the final pH value of the preparation solvent system is equal or below 2 after addition of the acid.

A catalyst composition in the context of the present specification refers particularly to a compound or composition that can lower the activation energy of a chemical reaction and accelerate the reaction by at least 3 orders of magnitude, particularly a hydrogenation reaction in presence of elementary hydrogen. An optically inactive ligand in the context of the present specification refers to a compound that is capable of binding to the metal atom described above and that has no optical activity.

In some embodiments, the optically inactive ligand is selected from the group comprised of 1,5-cyclooctadiene, acetyl acetonate, (1,5-cyclooctadien)bismethylallyl, bis(ethylcyclopentadienyl), bis(pentamethylcyclopentadienyl), p-cymene, diacetato, norbonadiene, cyclohexadiene, cylcoheptandiene, para-methadiene, α-Phellandiene and benzol.

The terms optically active ligand, acid, solubilizer, surfactant and micelle have the same meaning as described above.

In some embodiments, the solubilizer is a polar organic solvent miscible in water over a range of 1 part solvent:99 parts water to 1 part solvent:5 parts water.

In some embodiments, the solubilizer is a preparation surfactant that is capable of forming micelles in water and resistant to hydrolysis at pH 2.

In some embodiments, the preparation solvent system comprises not more than 50% (v/v), 25% (v/v), 20% (v/v), 10% (v/v) or 1% (v/v) polar organic solvent.

In some embodiments, the preparation solvent system comprises at least (≥)25% (v/v), ≥50% (v/v), ≥75% (v/v) ≥80% (v/v), ≥90% (v/v), ≥99% (v/v) or 100% (v/v) water.

In some embodiments, the second catalyst composition further comprises a water molecule bound to the ruthenium atom. The nature of the bond between the ruthenium atom and the water molecule is covalent or coordinative in nature.

In some embodiments, the second catalyst composition comprises two water molecules bound to the ruthenium atom.

In some embodiments, the second catalyst composition is further reacted with elementary hydrogen, yielding a catalyst composition with a monohydride bound to the ruthenium atom.

The nature of the bond between the ruthenium atom and the monohydride is covalent or coordinative in nature.

Suchsecond catalyst composition is suitable to perform a catalytic cycle as described above.

In some embodiments, the preparation surfactant is provided in the preparation solvent system in a concentration equal or above the surfactant's critical micelle concentration.

In some embodiments, the second catalyst composition is insoluble in water.

In some embodiments, the preparation solvent system further comprises a pH-control agent.

A pH-control agent in the context of the present specification refers to a compound by which the pH of an aqueous solution can be altered. Such pH-control agent may be an acid, a base or ion exchange resin. A pH control agent may also be a buffer system comprising a combination of acids and bases that are selected such that the pH value of a composition comprising the buffer changes less upon addition of an acid or a base than in a corresponding composition without the buffer system.

In some embodiments, the preparation surfactant has a critical micellar concentration (CMC) value of ≤10 mM, more preferably ≤1 mM, most preferably ≤0.25 mM, wherein CMC specifies the lowest concentration of the surfactant in water at which spherical micelles are formed at 25° C. and 1 bar.

In some embodiments, the preparation surfactant is non-ionic.

In some embodiments, the preparation surfactant is an alkylglycoside. The term alkylglycoside has the same meaning as described above.

In some embodiments, the preparation surfactant is D-Glycopyranoside C9-C11 alkyl (CAS No. 132778-08-6, obtained from Cognis/BASF AG).

In some embodiments, the acid is characterized by a pKa value of <0.

In some embodiments, the acid is a hydrogen acid.

In some embodiments, the acid is characterized by formula HX, wherein X is the corresponding anionic base.

In some embodiments, the acid deprotonates after solving in the preparation solvent system, whereby the resulting corresponding anionic base of the acid binds to the ruthenium atom comprised within the second catalyst composition. The nature of the bond between the ruthenium atom and the corresponding anionic base is covalent or coordinative in nature.

In some embodiments, the acid is selected from the group comprised of sulphuric acid, nitric acid, sulfonic acid, perchloric acid, perbromic acid, fluorosulfuric acid, hydrobromic acid, hydrochloric acid, hydriodic acid, and fluoroboric acid.

In some embodiments, an acid solution is solved in the preparation solvent system, wherein the acid solution is characterized by a concentration of 0.1 N, 0.2 N, 0.3 N, 0.4 N, 0.5 N, 0.6 N, 0.7 N, 0.8 N, 0.9 N, 1 N, 1.5 N, 2 N, 2.5 N or 3 N.

According to third aspect of the invention, a method for hydrogenating a double bond in a substrate molecule is provided, the double bond being selected from the group comprised of C=O and C=N, wherein the method comprises the steps of:
a) providing a reaction solvent system comprising at least 25% (v/v) water, and
b) solving in the reaction solvent system a solubilizer, the substrate molecule and a catalyst composition comprising a ruthenium atom and an optically active ligand, wherein the optically active ligand is insoluble in water, characterized in that the hydrogenating is performed at pH 2.

Hydrogenating a double bond in context of the present specification refers to a chemical reaction, wherein the double bond is converted to a single bond and hydrogen is added to both partners of the former double bond.

In some embodiments, the substrate has a molecular mass of more (>) than 28, 34, 60 or 72 g/mol. In some embodiments, the substrate molecule is organic molecule comprising at least 5 atoms of a molecular mass of 12 or higher, and comprising a carbonyl (keto, aldehyde) or imine group.

The terms catalytic composition, solubilizer and optically active ligand have the same meaning as described above.

In some embodiments, the hydrogenation is performed at pH≤2 by further solving an acid in the reaction solvent system. The term acid has the same meaning as described above.

In some embodiments, the reaction solvent system comprises at least 50% (v/v), 75% (v/v) 80% (v/v), 90% (v/v), 99% (v/v) or 100% (v/v) water.

In some embodiments, the acid is a hydrogen acid.

In some embodiments, the acid is characterized by a pKa value of <0.

In some embodiments, the acid is selected from the group comprised of sulphuric acid, nitric acid, sulfonic acid, perchloric acid, perbromic acid, fluorosulfuric acid, hydrobromic acid, hydrochloric acid, hydriodic acid and fluoroboric acid.

In some embodiments, the solubilizer is a polar organic solvent or a reaction surfactant that is capable of forming a micelle in water and resistant to hydrolysis at pH 2. The term surfactant has the same meaning as described above.

In some embodiments, the reaction solvent system comprises not more than 50% (v/v), 25% (v/v), 20% (v/v), 10% (v/v) or 1% (v/v) polar organic solvent.

In some embodiments, the reaction surfactant is provided in the reaction solvent system in a concentration equal or above the surfactant's critical micelle concentration.

In some embodiments, the reaction surfactant has a critical micellar concentration (CMC) value of not larger than 10 mM, more preferably 1 mM, most preferably 0.25 mM, wherein CMC specifies the lowest concentration of the surfactant in water at which spherical micelles are formed at 25° C. and 1 bar.

In some embodiments, the reaction surfactant is non-ionic.

In some embodiments, the reaction surfactant is an alkylglycoside. The term alkylglycoside has the same meaning as described above.

In one embodiment, the reaction surfactant is D-Glycopyranoside C9-C11 alkyl (CAS No. 132778-08-6, obtained from Cognis/BASF AG).

In some embodiments, the reaction surfactant is identical to the preparation surfactant described above.

In some embodiments, the substrate molecule comprises at least 3 carbon atoms.

In some embodiments, the substrate molecule is soluble in the aqueous phase of the reaction solvent system.

In some embodiments, the substrate molecule is an aliphatic or cyclic, saturated or unsaturated compound having a carbonyl or imine group such ketones, aldehydes, aldimines, ketimines, cabon acid or esters.

In some embodiments, the reaction solvent system further comprises a pH-control agent. The term pH-control agent has the same meaning as described above.

In some embodiments, the hydrogenation is performed at temperatures between 20° C. and 200° C., preferably between 80° C. and 180° C., more preferably between 100° C. and 140° C., most preferable between 110° C. and 130° C.

In some embodiments, the reaction solvent system does not comprise organic solvents.

In some embodiments, the hydrogenating is an asymmetric hydrogenating reaction. Asymmetric hydrogenating in the context of the present specification shall mean that adding hydrogen to the double bond of a substrate molecule generates a new chiral centre, and that the asymmetric adding results in an addition product in enantiomeric excess (ee) of 50%, 90% or 95%. Enantiomeric excess is defined as the absolute difference between the mole fraction of each enantiomer. For example an enantiomeric excess of 90% means an addition product with 95 n/n % of one enantiomer and 5 n/n % of the opposite enantiomer.

In some embodiments, the catalyst composition is obtained by a method according to the second aspect or comprises an active catalyst complex obtained by a method according to the first aspect of the invention.

In some embodiments, the method for hydrogenating a double bond further comprises solving an acid in the reaction solvent system.

In some embodiments, the acid is a hydrogen acid.

In some embodiments, the acid is selected from the group comprised of sulphuric acid, nitric acid, sulfonic acid, perchloric acid, perbromic acid, fluorosulfuric acid, hydrobromic acid, hydrochloric acid, hydriodic acid and fluoroboric acid.

In some embodiments, an acid solution is solved in the reaction solvent system, wherein the acid solution is characterized by a concentration of 0.1 N, 0.2 N, 0.3 N, 0.4 N, 0.5 N, 0.6 N, 0.7 N, 0.8 N, 0.9 N, 1 N, 1.5 N, 2 N, 2.5 N or 3 N.

In some embodiments, the substrate molecule is selected from the group comprised of:

hydroxyacetone (1-hydroxypropan-2-one):

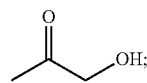

2,4 pentadione:

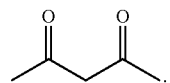

In some embodiments, the product of the hydrogenating is selected from the group comprised of:

(2R)-propane-1,2-diol:

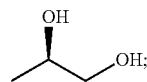

(2S)-propane-1,2-diol:

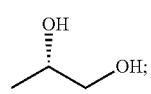

(2R,4R)-pentane-2,4-diol:

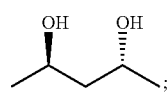

(2S,4S)-pentane-2,4-diol:

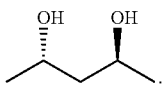

According to fourth aspect of the invention, a reaction mixture is provided, comprising
- a solvent system comprising at least 25% water,
- a solubilizer,
- an active catalyst complex as specified in the first aspect of the invention or a catalyst composition as specified in the second aspect of the invention, and
- a substrate molecule comprising a double bond selected from C=O and C=N.

The terms solubilizer, surfactant, reaction surfactant, catalyst complex, catalyst composition and substrate molecule have the same meaning as described above.

In some embodiments, the solvent system comprises at least 50%, at least 75% or at least 95% water or at least 100% water.

In some embodiments, the solubilizer is a polar organic solvent or a reaction surfactant as specified in the above embodiments.

In some embodiments, the solvent system comprises not more than 50% (v/v), 25% (v/v), 20% (v/v), 10% (v/v) or 1% (v/v) polar organic solvent. In some embodiments, the reaction mixture does not comprise organic solvents.

In some embodiments, the substrate molecule is any of hydroxyacetone (1-hydroxypropan-2-one):

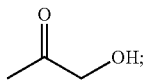

2,4 pentadione:

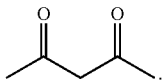

Wherever reference is made herein to an embodiment of the invention, and such embodiment only refers to one feature of the invention, it is intended that such embodiment may be combined with any other embodiment referring to a different feature. For example, every embodiment that defines an optically active ligand may be combined with every embodiment that defines S, $R^1$, $R^2$ or X to characterize a group of precatalyst or active catalyst complexes or compositions of the invention or a single complex or composition of the invention with different properties.

The invention is further characterized, without limitations, by the following examples, from which further features, advantages or embodiments can be derived. The examples do not limit but illustrate the invention.

EXAMPLES

Preparation Method I $6.0144*10^{-5}$ mol of (1,5-cyclooctadiene)bismethylallyl-ruthenium and 1.1 equivalents of the chiral ligand (such as e.g. SYNPHOS or SEGPHOS) were dissolved in 5 ml ethanol under nitrogen atmosphere. 2.2 equivalents of a 0.18 N solution of hydrobromic acid in methanol was added and stirred for 30 minutes at room temperature. Thus, the final concentration of hydrobromic acid was 0.0001323 mol in 5 ml ethanol, which equates to a pH value of 1.57.

Preparation Method II. Catalyst Preparation with Pure Hydrobromic Acid $6.0144*10^{-5}$ mol of (1,5-cyclooctadiene)bismethylallyl-ruthenium and 1.1 equivalents of the chiral ligand were dissolved in 5 ml ethanol under nitrogen atmosphere. 2.2 equivalents of 0.18 N hydrobromic acid solution was added and stirred for 50 minutes at room temperature. Thus, the final concentration of hydrobromic acid was 0.0001323 mol in 5 ml ethanol, which equates to a pH value of 1.57.

Preparation Method III. Catalyst Preparation without Organic Solvents 100 mg of alkylpolyglucoside were dissolved in 5 ml of degassed water. 27.5 µl of a 45 wt. % hydrobromic acid solution were added. $6.0144*10^{-5}$ mol of (1,5-cyclooctadiene)bismethylallylruthenium and 1.1 equivalents of the chiral ligand were dissolved in the aqueous surfactant solution and stirred for 30-50 minutes at room temperature. Thus, the final concentration of hydrobromic acid was 0.000153 mol in 5 ml water, which equates to a pH value of 1.5.

Working Example 1

The catalyst solution obtained according to Preparation III, but with (S)-SYNPHOS as chiral ligand was placed into an autoclave in the presence of 50 ml of ethanol, 275 µl of a 45 wt. % hydrobromic acid solution as well as $5.4*10^{-3}$ mol of hydroxyacetone under a hydrogen atmosphere of 1.1 bar pressure. Thus, the final concentration of hydrobromic acid was 0.0456 mol/l, which equates to a pH value of 1.34. The reaction mixture was stirred and heated at 60° C. for 1 hour. The enantiomeric excess was then determined by chiral GC (FS LIPODEX A column). As a result, the yield was 100% and the purity of the (S)-form of 1,2-propanediol was more than 97% ee.

Working Example 2

The catalyst solution obtained according to Preparation III, but with (S)-SYNPHOS as chiral ligand was placed into an autoclave in the presence of 50 ml of degassed water, 275 µl of a 45 wt. % hydrobromic acid solution, 1 g alkylpolyglucoside as well as $5.4*10^{-3}$ mol of hydroxyacetone under a hydrogen atmosphere of 4.2 bar pressure. Thus, the final concentration of hydrobromic acid was 0.0456 mol/l, which equates to a pH value of 1.34. The reaction mixture was stirred and heated at 125° C. for 6 hours. The solution was extracted with ethyl acetate. The extract was dried on anhydrous magnesium sulfate. The enantiomeric excess was then determined by chiral GC (FS LIPODEX A). As a result, the yield was 100% and the purity of the (S)-form of 1,2-propanediol was more than 97% ee.

Working Example 3

The catalyst solution obtained according to Preparation II, but with (S)-SEGPHOS as chiral ligand was placed into an autoclave in the presence of 50 ml of degassed water, 275 µl of a 45 wt. % hydrobromic acid solution, 1 g alkylpolyglucoside as well as 5.4*10$^{-3}$ mol of hydroxyacetone under a hydrogen atmosphere of 4.2 bar pressure. Thus, the final concentration of hydrobromic acid was 0.044 mol/l, which equates to a pH value of 1.36 The reaction mixture was stirred and heated at 125° C. for 3 hours. The solution was extracted with ethyl acetate. The extract was dried on anhydrous magnesium sulfate. The enantiomeric excess was then determined by chiral GC as in Example 1. As a result, the conversion was 55% and the purity of the (S)-form of 1,2-propanediol was more than 97% ee, by a yield of 100% (i.e. 100% of the 55% of the starting materials which were converted belong to the desired product species, which means that no side reactions occurred; the product showed an enantiomeric excess of 97% ee).

Working Example 4

The catalyst solution obtained according to Preparation II, but with (R)-SYNPHOS as chiral ligand is placed into an autoclave in the presence of, 30 ml of heptane, 20 ml of degassed water, 110 µl of a 45 wt. % hydrobromic acid solution, 1 g alkylpolyglucoside as well as 5.4*10$^{-3}$ mol of hydroxyacetone under a hydrogen atmosphere of 4.7 bar pressure. Thus, the final concentration of hydrobromic acid was 0.019 mol/l, which equates to a pH value of 1.72. The reaction mixture was stirred and heated at 125° C. for 3 hours. The solution was extracted with ethyl acetate. The extract was dried on anhydrous magnesium sulfate. The enantiomeric excess was then determined by chiral GC as in Example 1. As a result, the yield was 90% and the purity of the (R)-form of 1,2-propanediol was more than 97% ee.

Working Example 5

The catalyst solution obtained according to Preparation II, but with (S)-SYNPHOS as chiral ligand is placed into an autoclave in the presence of, 25 ml of ethanol, 30 ml of degassed water, 165 µl of a 45 wt. % hydrobromic acid solution, 2 ml alkylpolyglucoside as well as 0.51 g of hydroxyacetone under a hydrogen atmosphere of 1.1 bar pressure. Thus, the final concentration of hydrobromic acid was 0.025 mol/l, which equates to a pH value of 1.6. The reaction mixture was stirred and heated at 60° C. for 6 hours. The solution was extracted with ethyl acetate. The extract was dried on anhydrous magnesium sulfate. The enantiomeric excess was then determined by chiral GC as in Example 1. As a result, the yield was 100% and the purity of the (S)-form of 1,2-propanediol was more than 97% ee.

Working Example 6

The catalyst solution obtained according to Preparation I, but with (S)-SEGPHOS as chiral ligand was placed into an autoclave in the presence of, 25 ml of ethanol, 30 ml of degassed water, 165 µl of a 45 wt. % hydrobromic acid solution, 2 ml alkylpolyglucoside as well as 0.51 g of hydroxyacetone under a hydrogen atmosphere of 1.1 bar pressure. Thus, the final concentration of hydrobromic acid was 0.025 mol/l, which equates to a pH value of 1.6. The reaction mixture was stirred and heated at 60° C. for 3 hours. The solution was extracted with ethyl acetate. The extract was dried on anhydrous magnesium sulfate. The enantiomeric excess was then determined by chiral GC as in Example 1. As a result, the yield was 100% and the purity of the (S)-form of 1,2-propanediol was more than 97% ee.

Working Example 7

The catalyst solution obtained according to Preparation III, but with (S)-SYNPHOS as chiral ligand was placed into an autoclave in the presence of, 25 ml of ethanol, 30 ml of degassed water, 165 µl of a 45 wt. % hydrobromic acid solution, 2 ml alkylpolyglucoside as well as 0.51 g of hydroxyacetone under a hydrogen atmosphere of 1.1 bar pressure. Thus, the final concentration of hydrobromic acid was 0.0266 mol/l, which equates to a pH value of 1.57. The reaction mixture was stirred and heated at 60° C. for 3 hours. The solution was extracted with ethyl acetate. The extract was dried on anhydrous magnesium sulfate. The enantiomeric excess was then determined by chiral GC as in Example 1. As a result, the conversion was 100% and the purity of the (S)-form of 1,2-propanediol was more than 97% ee.

Working Example 9

The catalyst solution obtained according to Preparation I, but with (S)-SYNPHOS as chiral ligand was placed into an autoclave in the presence of, 25 ml of ethanol, 30 ml of degassed water, 165 µl of a 45 wt. % hydrobromic acid solution, 2 ml alkylpolyglucoside as well as 0.51 g of hydroxyacetone under a hydrogen atmosphere of 1.1 bar pressure. The reaction mixture was stirred and heated at 60° C. for 3 hours. Thus, the final concentration of hydrobromic acid was 0.025 mol/l, which equates to a pH value of 1.6. The solution was extracted with ethyl acetate. The extract was dried on anhydrous magnesium sulfate. The enantiomeric excess was then determined by chiral GC as in Example 1. As a result, the conversion was 91% and the purity of the (S)-form of 1,2-propanediol was more than 97% ee.

Working Example 9

The catalyst solution obtained according to Preparation II, but with (S)-SYNPHOS as chiral ligand is placed into an autoclave in the presence of, 25 ml of ethanol, 37.5 ml of degassed water, 165 µl of a 45 wt. % hydrobromic acid solution, 2 ml alkylpolyglucoside as well as 0,428 g of hydroxyacetone under a hydrogen atmosphere of 1.1 bar pressure. Thus, the final concentration of hydrobromic acid was 0.022 mol/l, which equates to a pH value of 1.65. The reaction mixture was stirred and heated at 80° C. for 6 hours. The solution was extracted with ethyl acetate. The extract was dried on anhydrous magnesium sulfate. The enantiomeric excess was then determined by chiral GC as in Example 1. As a result, the conversion was 90% and the purity of the (S)-form of 1,2-propanediol was more than 97% ee.

Working Example 10

The catalyst solution obtained according to Preparation III, but with (S)-SYNPHOS as chiral ligand is placed into an autoclave in the presence of, 25 ml of ethanol, 37.5 ml of degassed water, 165 µl of a 45 wt. % hydrobromic acid solution, 2 ml alkylpolyglucoside as well as 0,428 g of hydroxyacetone under a hydrogen atmosphere of 1.1 bar pressure. Thus, the final concentration of hydrobromic acid was 0.0236 mol/l, which equates to a pH value of 1.63. The reaction mixture was stirred and heated at 80° C. for 6 hours. The solution was extracted with ethyl acetate. The extract was dried on anhydrous magnesium sulfate. The enantiomeric excess was then determined by chiral GC as in Example 1. As a result, the conversion was 90% and the purity of the (S)-form of 1,2-propanediol was more than 97% ee.

Working Example 11

The catalyst solution obtained according to Preparation III, but with (S)-SYNPHOS as chiral ligand was placed into an autoclave in the presence of 30 ml of heptane, 20 ml of degassed water, 110 µl of a 45 wt. % hydrobromic acid solution, 1 g alkylpolyglucoside as well as $5.4*10^{-3}$ mol of hydroxyacetone under a hydrogen atmosphere of 4.7 bar pressure. Thus, the final concentration of hydrobromic acid was 0.0455 mol/l, which equates to a pH value of 1.34. The reaction mixture was stirred and heated at 125° C. for 3 hours. The solution was extracted with ethyl acetate. The extract was dried on anhydrous magnesium sulfate. The enantiomeric excess was then determined by chiral GC as in Example 1. As a result, the conversion was 90% and the purity of the (S)-form of 1,2-propanediol was more than 97% ee.

Working Example 12

The catalyst solution obtained according to Preparation III, but with (R)-SYNPHOS as chiral ligand was placed into an autoclave in the presence of 30 ml of heptane, 20 ml of degassed water, 110 µl of a 45 wt. % hydrobromic acid solution, 1 g alkylpolyglucoside as well as $5.4*10^{-3}$ mol of 2,4-pentanedione under a hydrogen atmosphere of 4.7 bar pressure. Thus, the final concentration of hydrobromic acid was 0.0455 mol/l, which equates to a pH value of 1.34. The reaction mixture was stirred and heated at 125° C. for 6 hours. The solution was extracted with ethyl acetate. The extract was dried on anhydrous magnesium sulfate. The enantiomeric excess was then determined by chiral GC as in Example 1. As a result, the conversion was 90% and the purity of the (R,R)-form of 2,4-pentanediol was more than 99% ee.

The invention claimed is:

1. A method for converting a precatalyst complex to an active catalyst complex,
    wherein said precatalyst complex and said active catalyst complex comprise a ruthenium atom and an optically active ligand that is insoluble in water, and
    wherein said active catalyst complex comprises a monohydride and a water molecule, said method comprising the steps of:
a) providing an activation solvent system comprising water,
b) adding to, particularly solving in, said activation solvent system
    said precatalyst complex,
    a solubilizer,
    an acid, and
    hydrogen,
characterized in that
the pH value of said activation solvent system is equal or below 2 after addition of said acid.

2. The method according to claim 1, wherein said activation solvent system comprises ≥50% (v/v), ≥75% (v/v), ≥80% (v/v), ≥90% (v/v), ≥99% (v/v) or 100% water.

3. The method according to claim 1, wherein said solubilizer is a surfactant that is capable of forming micelles in water and that is resistant to hydrolysis at pH≤2.

4. The method according to claim 1, wherein said optically active ligand is selected from the group consisting of:
5,5'-bis(diphenylphosphino)-4,4'-bi-1,3-benzodioxane;
(5,5'-bis(diphenylphosphino)-4,4'-bi-1,3-benzodioxole;
2,2'-bis(diphenylphosphino)-1,1'-binaphthyl;
O-isopropyliden-2,3-dihydroxy-1,4-bis(diphenylphosphino)butane;
ethane-1,2-diylbis[(2-methoxyphenyl)phenylphosphane];
(bis(diphenylphosphino)butane;
(3-diphenylphosphanyl-2-bicyclo[2.2.1]hept-5-enyl)-diphenyl-phosphane;
(1-benzyl-4-diphenylphosphanyl-pyrrolidin-3-yl)-diphenyl-phosphane;
(2-diphenylphosphanyl-1-methyl-ethyl)-diphenyl-phosphane;
[2-(diphenylphosphanylmethyl)cyclohexyl]methyl-diphenyl-phosphane;
tert-butyl 4-benzhydryl-2-(2,2-diphenylethyl)pyrrolidine-1-carboxylate;
[2-(1-naphthyl)phenyl]-[2-[2-(1-naphthyl)phenyl]phosphanylethyl]phosphane,
[2-(2-diphenylphosphanyl-6-methoxy-phenyl)-3-methoxy-phenyl]-diphenyl-phosphane;
[4-chloro-2-(3-chloro-6-diphenylphosphanyl-2-methoxy-phenyl)-3-methoxy-phenyl]-diphenyl-phosphane;
[5-chloro-2-(4-chloro-2-diphenylphosphanyl-6-methoxy-phenyl)-3-methoxy-phenyl]-diphenyl-phosphane;
[2-(6-diphenylphosphanyl-2,3,4-trimethyl-phenyl)-3,4,5-trimethyl-phenyl]-diphenyl-phosphane;
[3-(4-diphenylphosphanyl-2,6-dimethoxy-3-pyridyl)-2,6-dimethoxy-4-pyridyl]-diphenyl-phosphane;
[4-(4-diphenylphosphanyl-2,5-dimethyl-3-thienyl)-2,5-dimethyl-3-thienyl]-diphenyl-phosphane;
[8-(7-diphenylphosphanyl-4-methyl-2,3-dihydro-1,4-benzoxazin-8-yl)-4-methyl-2,3-dihydro-1,4-benzoxazin-7-yl]-diphenyl-phosphane; and
a compound characterized by formula III:

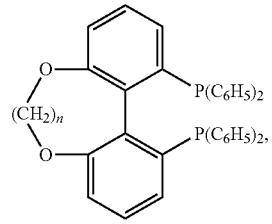

(III)

wherein n is 1, 2, 3, 4, 5 or 6.

* * * * *